(12) United States Patent
Khalili et al.

(10) Patent No.: US 6,187,050 B1
(45) Date of Patent: Feb. 13, 2001

(54) OBLONG ACETABULAR CUP

(75) Inventors: Farid Bruce Khalili, Chestnut Hill; Pierre S. Ostiguy, Jr., Rochester; Robert E. Sommerich, Norton, all of MA (US)

(73) Assignee: Johnson & Johnson Professional, Inc., Raynham, MA (US)

( * ) Notice: Under 35 U.S.C. 154(b), the term of this patent shall be extended for 0 days.

(21) Appl. No.: 08/998,909

(22) Filed: Dec. 29, 1997

(51) Int. Cl.$^7$ .................................................. A61F 2/34
(52) U.S. Cl. .............................. 623/22.22; 623/22.31; 623/22.38
(58) Field of Search ................... 623/22, 18, 22.21, 623/22.22, 22.23, 22.31, 22.32, 22.38

(56) References Cited

U.S. PATENT DOCUMENTS

| | | | |
|---|---|---|---|
| D. 296,714 | 7/1988 | Averill et al. | D24/33 |
| 3,744,061 | 7/1973 | Frost | 3/1 |
| 3,891,997 | 7/1975 | Herbert | 3/1 |
| 4,634,444 | 1/1987 | Noiles | 623/20 |
| 4,662,891 | 5/1987 | Noiles | 623/22 |
| 4,678,472 | 7/1987 | Noiles | 623/1.8 |
| 4,695,282 | 9/1987 | Forte et al. | 623/22 |
| 4,704,127 | 11/1987 | Averill et al. | 623/22 |
| 4,798,610 | 1/1989 | Averill et al. | 623/22 |
| 4,846,839 | 7/1989 | Noiles | 623/18 |
| 4,865,603 | 9/1989 | Noiles | 623/18 |
| 4,892,549 | 1/1990 | Figgie, III et al. | 623/22 |
| 4,950,299 | 8/1990 | Noiles | 623/22 |
| 4,978,356 | 12/1990 | Noiles | 623/18 |
| 5,176,711 * | 1/1993 | Grimes | 623/22 |
| 5,192,329 | 3/1993 | Christie et al. | 623/22 |
| 5,282,864 | 2/1994 | Noiles et al. | 623/18 |
| 5,290,315 | 3/1994 | DeCarlo, Jr. | 623/22 |
| 5,314,488 | 5/1994 | Hayashi et al. | 623/22 |
| 5,358,532 | 10/1994 | Evans et al. | 623/22 |
| 5,370,704 | 12/1994 | DeCarlo, Jr. | 623/22 |
| 5,413,603 | 5/1995 | Noiles et al. | 623/18 |
| 5,549,694 | 8/1996 | Noiles et al. | 623/22 |
| 5,549,697 | 8/1996 | Caldarise | 623/22 |
| 5,549,698 | 8/1996 | Averill | 623/22 |
| 5,549,701 | 8/1996 | Mikhail | 623/22 |
| 5,571,201 | 11/1996 | Averill et al. | 623/22 |
| 5,676,704 | 10/1997 | Ries et al. | 623/18 |
| 5,931,870 * | 8/1999 | Cuckler et al. | 623/16 |

FOREIGN PATENT DOCUMENTS

| | | | |
|---|---|---|---|
| 4442559 | 6/1995 | (DE) | A61F/2/34 |
| 2758255 | 7/1998 | (FR) | A61F/2/34 |
| 9817206 | 4/1998 | (WO) | A61F/2/34 |

* cited by examiner

*Primary Examiner*—Mickey Yu
*Assistant Examiner*—Tram A. Nguyen
(74) *Attorney, Agent, or Firm*—Nutter, McClennen & Fish, LLP

(57) ABSTRACT

An acetabular cup having an outer surface elongated in a superior/lateral direction is effective to anatomically transfer load to the acetabulum and reduce the likelihood of bone fracture during implantation into the acetabulum. The outer surface has a first portion defined by a first radius and a second portion defined by a second radius. The second radius is offset from the first radius in superior and lateral directions to elongate the outer surface of the acetabular cup.

14 Claims, 3 Drawing Sheets

OBLONG ACETABULAR CUP

CROSS REFERENCE TO RELATED APPLICATION

Not Applicable.

STATEMENT REGARDING FEDERALLY SPONSORED RESEARCH

Not Applicable.

FIELD OF THE INVENTION

The present invention relates to prosthetic components used in joint arthroplasty, and more particularly to an acetabular cup having enhanced implantation and fixation properties within the acetabulum of a patient.

BACKGROUND OF THE INVENTION

Joint arthroplasty is a well known surgical procedure by which a diseased and/or damaged natural joint is replaced by a prosthetic joint. Joint arthroplasty is commonly performed for hips, knees, elbows, and other joints. The health and condition of the joint to be replaced dictate the type of prosthesis necessary to replace the natural joint. For example, in a total hip arthroplasty an acetabular cup is implanted in the acetabular cavity in the pelvis to replace the natural acetabulum. Replacement of the acetabulum is necessary when there is an inadequate articulation surface for a head or ball of a prosthetic femoral component.

To implant an acetabular cup, a cavity is reamed in the acetabulum. The acetabular cup is then inserted into the formed cavity and secured by mechanical means, interference fit, or by a combination thereof. The acetabular cup is positioned in the pelvis at a fixed orientation with respect to patient anatomy and should remain stable.

For an acetabular cup relying upon an interference fit alone to secure the prosthesis, it is important that the cavity formed in the acetabulum be sufficiently undersized to provide adequate fixation of the acetabular cup. However, a spherical acetabular cup forcibly inserted into an undersized spherical cavity can, for some patients, result in unacceptable levels of hoop stress.

It is known in some instances that the bone at the cup/acetabulum interface can weaken over time, causing the position of the acetabular cup to shift. Such positional migration of the implanted acetabular cup can erode the surrounding bone of the acetabular cavity. The effect of such bone erosion is the loosening of the acetabular cup, allowing it to further shift in position. The end result of any positional displacement of the acetabular cup can be a non-optimal functioning of the joint or even dislocation of the joint.

Acetabular cup displacement can also generate wear debris, which can interfere with joint articulation. As the acetabular cup moves with respect to the pelvis, the implanted femoral head may no longer articulate within the acetabular cup within a desired range of motion. Improper positioning of the femoral head with respect to the acetabular cup can also accelerate the generation of wear debris creating a need for revision surgery.

Revision procedures in which the acetabular cup is replaced with a new prosthesis pose challenges as the replacement acetabular cup must be securely implanted in the pelvis. Bone erosion that typically necessitates such a revision procedure often produces an acetabular cavity having a shape that does not provide the most favorable conditions for an interference fit with many acetabular cups. Although bone grafts can be effected to reshape the acetabular cavity to be generally spherical, there are certain drawbacks to such bone grafts. For example, a suitable graft bone may not be readily available, it may be difficult to secure the bone graft to the existing bone, and the graft material may not provide sufficient mechanical strength.

Various methods and techniques are presently used to secure an acetabular cup in a cavity formed in the acetabulum of a patient. One such method includes the use of bone cement to secure the acetabular cup to the acetabulum. Another technique utilizes an acetabular cup having holes for receiving screws, or other such fasteners, to affix the acetabular cup to bone.

Acetabular cups with a variety of external geometries are known in the art. For example, U.S. Pat. No. 5,571,201 (Averill et al.) discloses an acetabular cup having a plurality of unidirectional steps for engaging bone. U.S. Pat. No. 5,192,329 (Christie et al.) discloses an oblong revision acetabular cup for implantation into an oblong cavity formed in the acetabulum. U.S. Pat. No. 5,676,704 (Ries et al.) discloses an acetabular cup having an outer surface that gradually thickens in a direction towards the rim of the acetabular cup.

Although, such acetabular cups are able to achieve some degree of fixation in the acetabulum of a patient, an acetabular cup is desired that provides long term fixation and transfers load to the acetabulum anatomically.

SUMMARY OF THE INVENTION

The present invention provides an acetabular cup having enhanced load transfer and bone fixation properties. In one embodiment, the acetabular cup is elongated in a superior/lateral direction. Although the invention is applicable to a variety of joint prostheses, it is primarily described in conjunction with an acetabular cup.

The acetabular cup has a concave, generally hemispherical inner surface and a generally convex outer surface with a pole and an equator. The outer surface has a first portion defined by a first radius originating from a first point and a second portion defined by a second radius originating from a second point. The second point is offset from the first point in superior and lateral directions such that the acetabular cup is elongated in a superior/lateral direction. In one embodiment, both the superior offset and the lateral offset of the second point from the first point are in the range from about 0.5 millimeter to about 3.0 millimeters.

To implant the elongated acetabular cup, a spherical cavity is reamed in the lunate region of the acetabulum of a patient. The acetabular cup is impacted into the formed cavity and secured therein by means of an interference fit. The asymmetrical contour of the elongated acetabular cup prevents excessive hoop stress concentration about the perimeter of the formed cavity. The likelihood of bone fractures during insertion of the acetabular cup is thereby reduced. The implanted acetabular cup also provides anatomic load transfer from the acetabular cup to the acetabulum.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
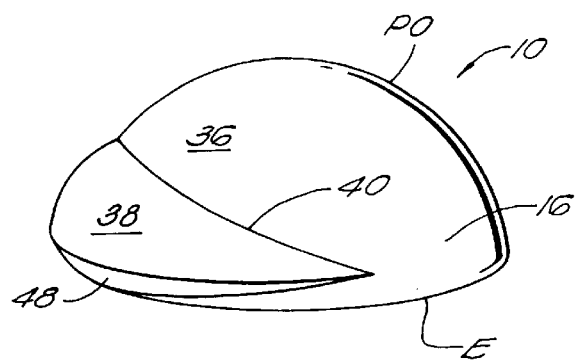
FIG. 1 is a perspective view of an acetabular cup in accordance with the present invention.

FIGS. 1–7 illustrate an exemplary acetabular cup 10 according to the present invention that is suitable for implantation in the acetabulum 12 of a patient. The acetabular cup 10 includes a concave, generally hemispherical inner surface 14 (FIG. 3) and a convex outer surface 16 that is elongated in a superior/lateral direction, as described below. The elongated configuration of the acetabular cup 10 is effective to provide ease of implantation and optimal performance. Further, the elongated acetabular cup of the invention is believed to be effective to anatomically transfer load to the acetabulum.

The acetabular cup 10 has a pole PO, at a top portion of its outer surface 16, and an equator region E opposite the pole PO. A first plane 18 (FIG. 2) divides the acetabular cup 10 into a superior portion 20 and an inferior portion 22 and a second plane 24 (FIG. 4) divides the acetabular cup into a medial portion 26 and a lateral portion 28. A third plane 30 (FIG. 3) splits the acetabular cup 10 into an anterior portion 32 and a posterior portion 34. The exemplary relative directions are indicated in the figures as follows: superior (S); inferior (I); medial (M); lateral (L); anterior (A); and posterior (P).

The outer surface 16 of the acetabular cup has a first portion 36 that forms a majority of the outer surface. The outer surface 16 also includes a second portion 38 offset from the first portion. The second portion 38 causes the shape of the first portion 36 to deviate from that of a hemisphere, yielding an outer surface that is elongated in superior and lateral directions. The first and second portions 36,38 of the outer surface intersect at a boundary 40 that extends from a point 40a (FIG. 5) on the anterior portion 32 of the outer surface to a point 40b on the posterior portion 34.

Figure 4:
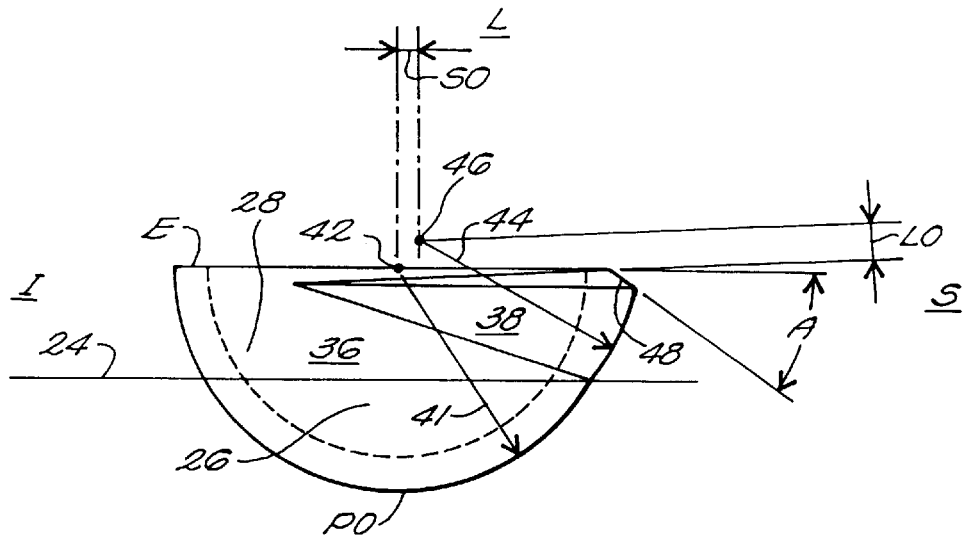
FIG. 4 is a side view of the acetabular cup of FIG. 1, in an inverted position.
Figure 5:
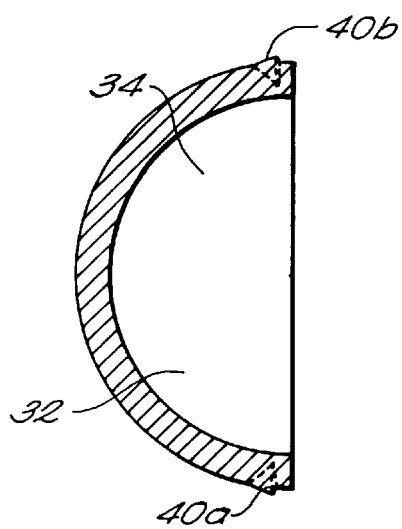
FIG. 5 is a cross-sectional view of the acetabular cup of FIG. 3 along lines 5—5.
Figure 6:
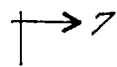
FIG. 6 is a front view of the acetabular cup of FIG. 1.
Figure 6:
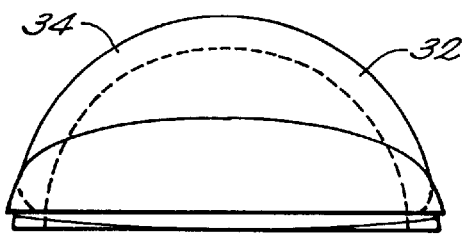
Figure 7:
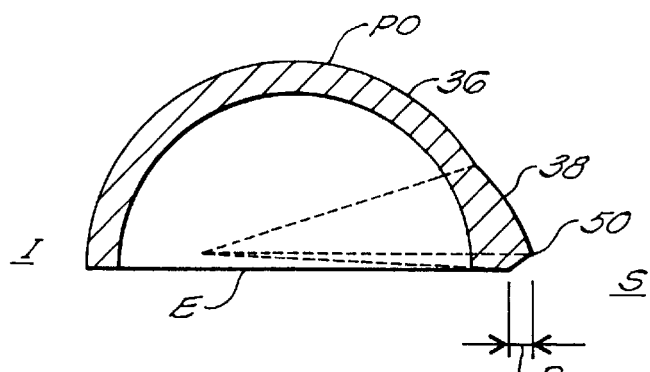
FIG. 7 is a cross-sectional view of the acetabular cup of FIG. 6 along lines 7—7.

As shown in FIG. 4, the first portion 36 of the outer surface is defined by a first radius 41 that originates from a first point 42 located on the equator E. The second portion 38 of the outer surface is defined by a second radius 44 originating from a second point 46 that is offset from the first point 42. In one embodiment, the second point 46 is offset from the first point 42 in superior and lateral directions. More particularly, the second point 46 is offset a distance SO in a superior direction and a distance LO in a lateral direction. The SO and LO offsets cause the outer surface 16 of the acetabular cup to be elongated in a superior/lateral direction. The elongation is most pronounced near the equator region E.

Figure 2:
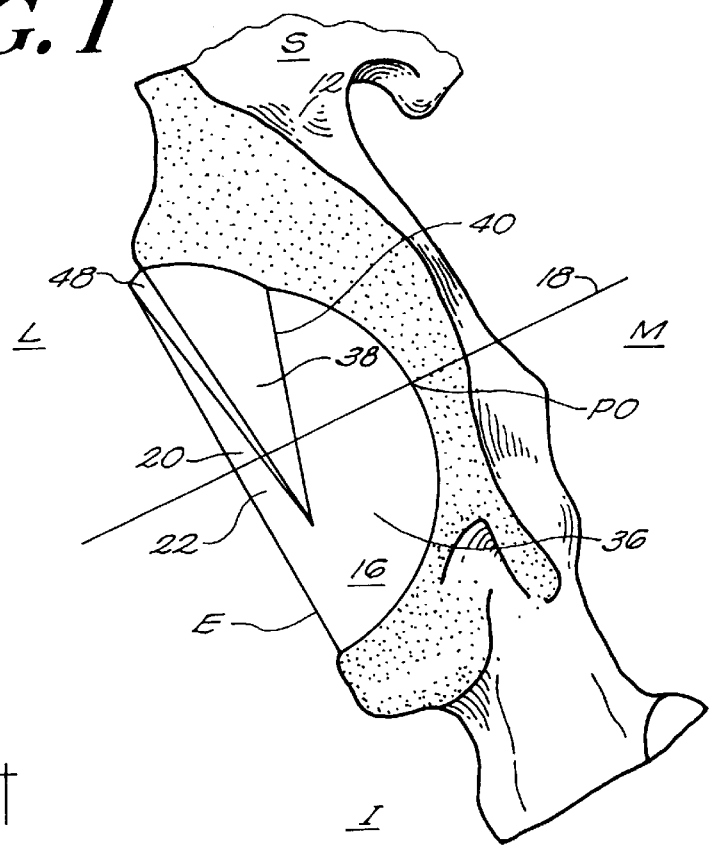
FIG. 2 is a side view of the acetabular cup of FIG. 1 shown implanted in an acetabulum.
Figure 3:
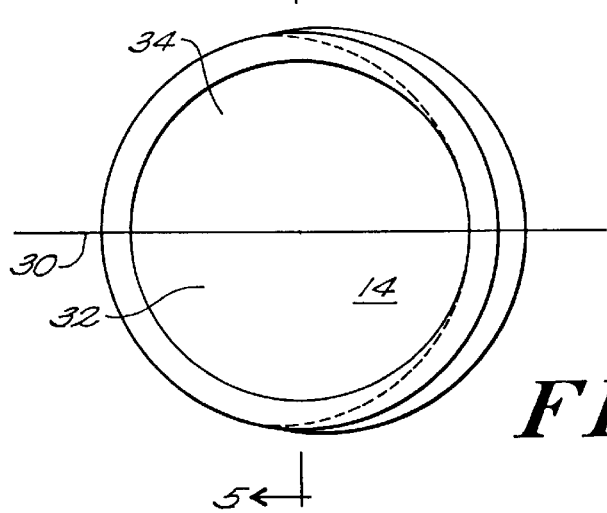
FIG. 3 is a bottom view of the acetabular cup of FIG. 1.

The second portion 38 generally is confined to the superior and lateral portions of the outer surface 16. That is, the second portion does not extend to the medial side of the axis 24 that divides the acetabular cup into medial and lateral portions. The second portion 38 may, however, extend slightly into the inferior portion of the shell, i.e., beyond axis 18 that separates superior and inferior portions of the acetabular cup. As shown in FIGS. 2–4, the second portion may extend into the inferior portion for a distance equal to about one third of the first radius 41.

FIG. 4 also illustrates a boundary surface 48, disposed between the second portion 38 and the equator region E. The boundary surface 48 provides a transition from the second portion 38 to the equator E. An angle A formed by the surface 48 with respect to the equator E can range from about zero degrees to about forty-five degrees. In one embodiment, the angle A is about thirty-five degrees.

The geometry of the outer surface 16 of the acetabular cup varies in accordance with the position of the superior and lateral offset of the origination points 42,46 and the respective lengths of the radii 41,44 that define the first and second portions 36,38 of the outer surface. For example, the first and second radii 41,44 can be of the same or different length. Alternatively, the second radius 44 can be shorter than the first radii provided that a desired elongation of the outer surface 16 in the superior/lateral direction is achieved.

In an exemplary embodiment, the first and second radii 41,44 that define the first and second portions 36,38 of the outer surface can have a length ranging from about 18 millimeters to about 45 millimeters, and more preferably between about 22 millimeters and about 30 millimeters. In one embodiment, the first radius 41 has a length of about 27 millimeters and the second radius 44 has a length of about 27 millimeters.

The offset of the second radius origination point 46 with respect to the first origination point 42 can vary to alter the amount of elongation of the acetabular cup. The superior offset SO ranges from about 0.5 millimeters to about 3.0 millimeters, and is preferably about 1.5 millimeters. The lateral offset LO also ranges from about 0.5 to about 5.0 millimeters with a preferred lateral offset of about 2.0 millimeters. It is understood that the superior and lateral offsets SO, LO are independent from each other.

The geometry of the outer surface 16 of the acetabular cup can vary to achieve a desired level of elongation, as described above. That is, the first and second radii 41,44 and the respective superior and lateral offsets SO, LO of the origination points 42,46 determine the elongation of the outer surface 16 of the acetabular cup. The elongation can be measured as the distance D (FIG. 7) along the superior direction from a tip 50 of the second portion 38 of the outer surface to the first portion 36 if extended to the equator region E, as shown. This elongation distance D is a measure of the degree of elongation that causes the shape of the outer surface 16 to depart from that of a hemisphere. The elongation distance D can range from about 0.5 millimeters to about 4.0 millimeters. In an exemplary embodiment the distance D is about 3.0 millimeters.

In addition to determining the elongation of the acetabular cup, the superior and lateral offsets SO, LO and radii 41,44 also apportion the surface area between the first and second portions 36,38 of the outer surface. However, the first portion 36 provides a majority of the total surface area of the outer surface 16, as described above.

It is understood that one of ordinary skill in the art can readily vary the geometry of the acetabular cup to accommodate different patient anatomies.

Figure 8:
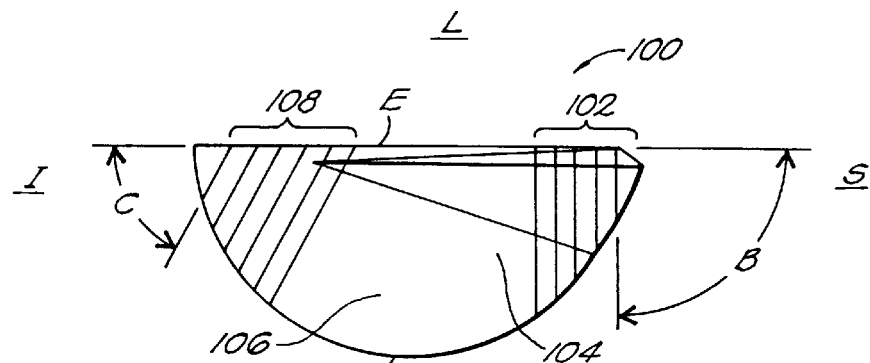
FIG. 8 is a side view of a further embodiment of an acetabular cup in accordance with the present invention.

In another embodiment shown in FIG. 8, an elongated acetabular cup 100 includes a first set of steps 102 formed in a superior portion 104 of the outer surface of the acetabular cup. First steps 102 extend from an anterior portion 106 to a posterior portion (not shown) of cup 100. Although shown as extending from a first point on equator region E to a second point thereon, it is understood that the steps 102 may extend from a point on the outer surface disposed above the equatorial plane E (i.e., toward the pole PO).

As shown, the first steps 102 form an angle B with respect to the equator E. The angle is less than or equal to 90 degrees, and typically is in the range of 75 to 90 degrees.

A second set of steps 108 is formed on an inferior portion of the acetabular cup. Typically, steps 108 extend from the anterior portion 106 to the posterior portion of the cup 100. The second steps 108 form an angle C with respect to the equator E. The angle B can vary from about 0 degrees to about 45 degrees, and typically is about 20 degrees.

Figure 9:
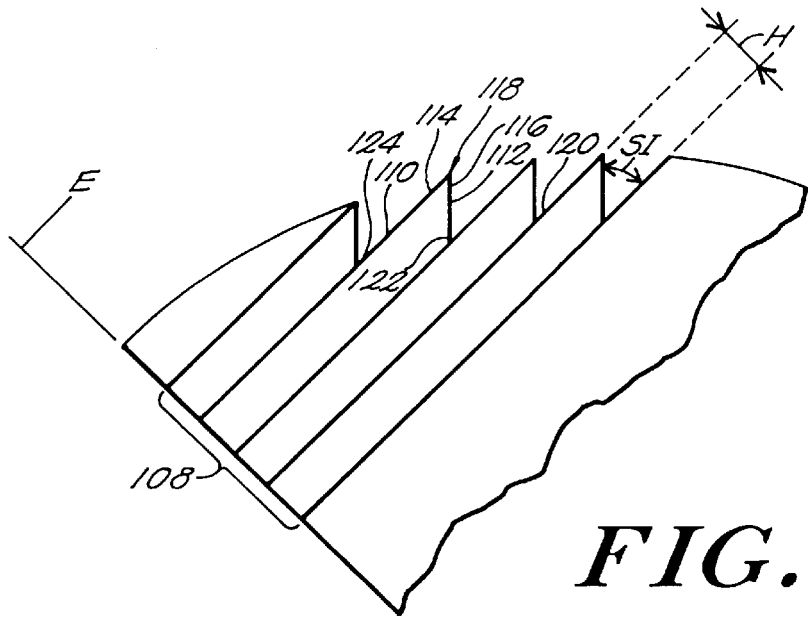
FIG. 9 is a partially cut-away detailed side view of a portion of the acetabular cup of FIG. 8.

As shown in FIG. 9, each step 108 has a superior surface 110 and an inferior surface 112. An end portion 114 of superior surface 110 joins an end portion 116 of inferior surface 112 to form a crest 118. Similarly, a rear portion 120 of superior surface 110 joins a rear portion 122 of inferior surface 112 to form groove 124. The superior surface 110 and inferior surface 112 of the steps form an angle SI and a height H, as shown.

An acetabular cup having bi-directional steps formed on an outer surface is disclosed in commonly assigned and co-pending U.S. patent application Ser. No. 08/975,604, filed on Nov. 21, 1997, and entitled: Acetabular Cup with Bi-Directional Steps, which is incorporated herein by reference.

To implant an acetabular cup of the present invention into the acetabulum, a generally spherical cavity is reamed in the acetabulum of a patient, preferably in the lunate region of the acetabulum. The formed spherical cavity has dimensions slightly smaller than the external dimensions of the acetabular cup so as to enable an interference fit of the acetabular cup. More particularly, the outer regions of the anterior and posterior portions of the formed cavity approach conformity with the complementary portions of the acetabular cup. In contrast, the elongated second portion 38 of the outer surface extends more significantly beyond the perimeter of the formed cavity. The elongated geometry of the acetabular cup distributes anterior/posterior stress on the acetabulum generated during forcible insertion of the acetabular cup to prevent or eliminate bone fractures.

Implantation of an acetabular cup elongated in a superior/lateral direction into a generally spherical cavity provides favorable conditions for long term fixation of the acetabular cup in the acetabulum. The elongated acetabular cup transfers joints loads to the acetabulum in a superior direction such that bone at the cup/acetabulum interface remains strong. The acetabular cup/bone interface emulates natural anatomic load transfer from the joint to the acetabulum.

The elongated geometry of the acetabular cup also reduces shifting of the center of the acetabulum as compared with a spherical implant. It is known that a proximal region of the natural acetabulum generally has thicker cartilage than other regions of the acetabulum. When implanted into the reamed acetabular cavity, the elongated acetabular cup compensates for the thicker cartilage region to recreate anatomic positioning of the acetabulum center.

One of ordinary skill in the art will appreciate that the acetabular cup of the present invention can be made from a variety of biocompatible materials having high strength and durability. Example of such materials include metal alloys as titanium alloys, cobalt chromium alloys, and stainless steel.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An acetabular cup, comprising:
   a generally hemispherical shell having a superior portion, an inferior portion, a medial portion, and a lateral portion, the shell further including a concave inner surface and a generally convex outer surface having a pole and an equator,
   wherein the outer surface has a first portion defined by a first radius originating from a first point centrally located proximate the equator and a second portion defined by a second radius originating from a second point offset from the first point in a superior and a lateral direction so as to form a superior offset and a lateral offset, such that the shell is elongated.

2. The acetabular cup according to claim 1, wherein the superior offset ranges from about 0.5 millimeter to about 3.0 millimeters and the lateral offset ranges from about 0.5 millimeter to about 5.0 millimeters.

3. The acetabular cup according to claim 1, wherein the first radius and the second radius are substantially the same length.

4. The acetabular cup according to claim 1, wherein the second radius has a length greater than a length of the first radius.

5. The acetabular cup according to claim 1, wherein the second radius has a length less than a length of the first radius.

6. The acetabular cup according to claim 1, wherein the first and second radii have a respective length between about 18 millimeters and about 45 millimeters.

7. The acetabular cup according to claim 1, further including a surface extending from a perimeter of the second portion of the outer surface to the equator.

8. The acetabular cup according to claim 7, wherein the surface forms an angle greater than zero degrees and less than or equal to about forty-five degrees with respect to the equator.

9. The acetabular cup according to claim 1, wherein, as compared with a hemisphere, the outer surface is elongated in the superior direction for a distance of between about 0.5 millimeters and about 4.0 millimeters along the equator.

10. The acetabular cup according to claim 1, wherein a plurality of steps are formed on the outer surface of the acetabular cup.

11. The acetabular cup according to claim 1, wherein a first set of steps are formed on the outer surface of the acetabular cup in a first direction and a second set of steps are formed on the outer surface in a second direction different than the first direction.

12. An acetabular cup, comprising;
    a concave inner surface; and
    a convex outer surface having a first portion defined by a first radius and a second portion defined by a second radius, the outer surface further having a superior portion, an inferior portion, a medial portion and a lateral portion,
    wherein the second portion effects an elongation of the outer surface of the acetabular cup in a superior/lateral direction, the elongation being defined by a superior offset and a lateral offset.

13. The acetabular cup according to claim 12, wherein the second portion elongates the outer surface a distance of about 3.0 millimeters in the superior direction.

14. The acetabular cup according to claim 12, wherein the first radius extends from a first radial point centrally located on a plane defined by a perimeter of the outer surface and the second radius extends from a second point offset from the first point in superior and lateral directions, wherein the superior offset ranges from about 0.5 millimeter to about 3.0 millimeters and the lateral offset ranges from about 0.5 millimeter to about 5.0 millimeters.

* * * * *